United States Patent [19]

Kasevich et al.

[11] Patent Number: 5,057,106
[45] Date of Patent: Oct. 15, 1991

[54] MICROWAVE BALLOON ANGIOPLASTY

[75] Inventors: Raymond S. Kasevich, Weston; James F. McQueeney, Natick; Ronald H. Crooker, Stoneham, all of Mass.

[73] Assignee: Kasevich Associates, Inc., Woburn, Mass.

[21] Appl. No.: 550,341

[22] Filed: Jul. 9, 1990

Related U.S. Application Data

[60] Continuation of Ser. No. 195,584, May 18, 1988, abandoned, which is a continuation-in-part of Ser. No. 100,465, Sep. 24, 1987, Pat. No. 4,776,086, which is a division of Ser. No. 834,199, Feb. 27, 1986, Pat. No. 4,700,716.

[51] Int. Cl.$^5$ .............................................. A61N 5/02
[52] U.S. Cl. ..................................... 606/33; 128/786; 128/804; 128/736
[58] Field of Search ................. 606/33; 128/736, 784, 128/786, 804, 401

[56] References Cited

U.S. PATENT DOCUMENTS

| | | |
|---|---|---|
| 4,583,556 | 4/1986 | Hines et al. . |
| 4,600,018 | 7/1986 | James et al. ........................ 128/804 |
| 4,612,940 | 9/1986 | Kasevich et al. . |
| 4,643,186 | 2/1987 | Rosen et al. ...................... 128/303.1 |
| 4,658,836 | 4/1987 | Turner . |
| 4,681,122 | 7/1987 | Winters et al. ...................... 128/736 |
| 4,700,716 | 10/1987 | Kasevich et al. .................. 128/804 |

FOREIGN PATENT DOCUMENTS

| | | |
|---|---|---|
| 105677 | 4/1984 | European Pat. Off. . |
| 0251745 | 1/1988 | European Pat. Off. ............ 128/804 |
| 1188490 | 4/1970 | United Kingdom ................ 128/804 |

Primary Examiner—Lee S. Cohen
Attorney, Agent, or Firm—Hale and Dorr

[57] ABSTRACT

A microwave catheter system used for heating arterial plaque and including a catheter member adapted for positioning in the artery and an inflatable balloon supported at the distal end of the catheter member. Microwave energy is coupled by means of a transmission line to an antenna means. An optic fiber extends through the catheter member and may be used for temperature sensing or other purposes. A channel is provided through the catheter member for coupling a fluid to the balloon for inflation thereof.

38 Claims, 10 Drawing Sheets

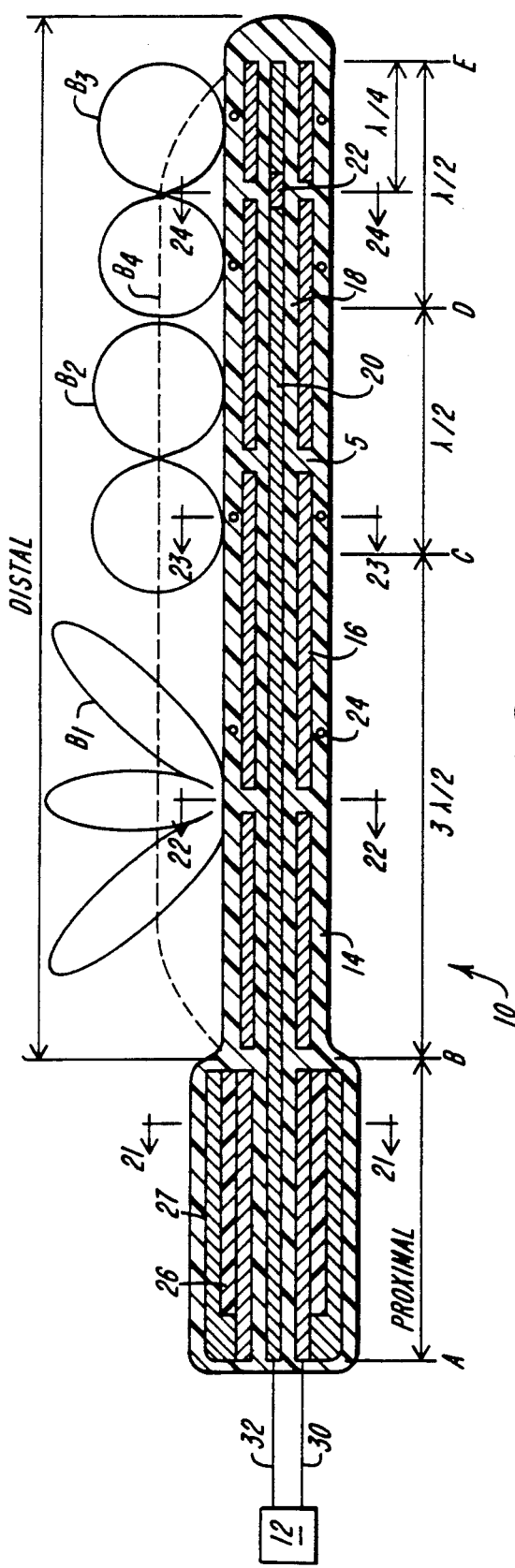
FIG. 20  FIG. 21  FIG. 22  FIG. 23  FIG. 24

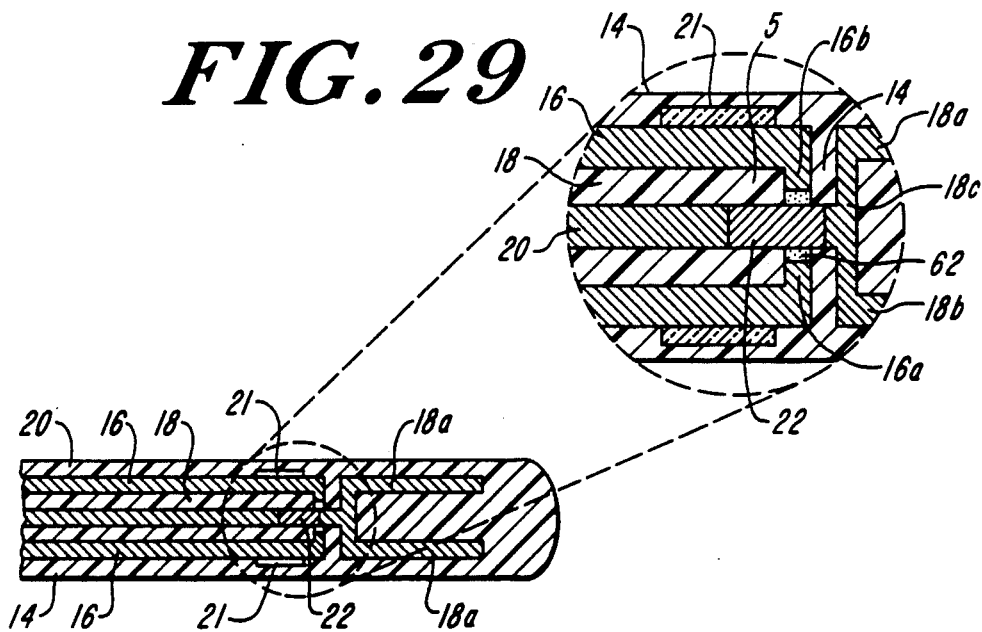
FIG. 29
FIG. 28
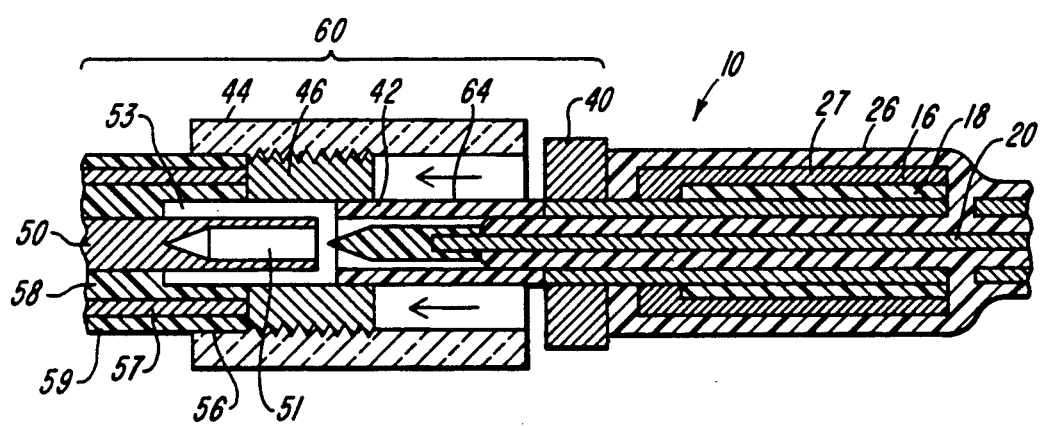
FIG. 30

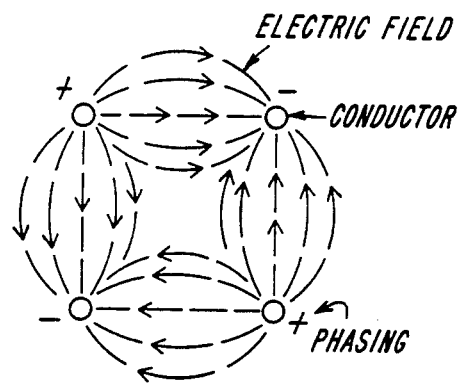
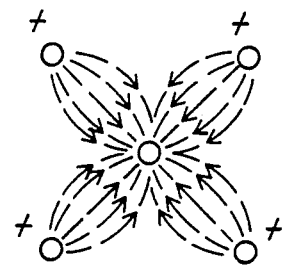
*FIG. 31*  *FIG. 32*
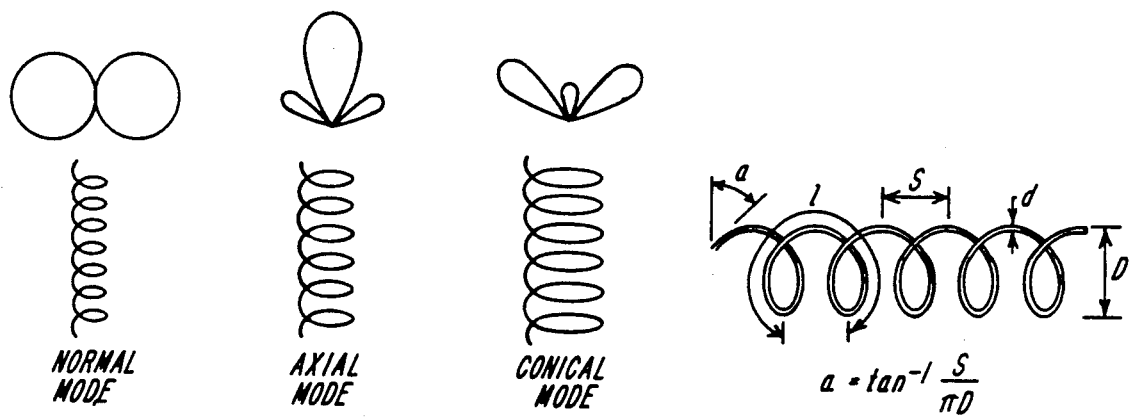
*FIG. 33*

MICROWAVE BALLOON ANGIOPLASTY

RELATED APPLICATIONS

This is a continuation of co-pending application Ser. No. 195,584 filed on 05/18/88, now abandoned which is a continuation-in-part of application Ser. No. 100,465, filed on Sept. 24, 1987, which in turn is a divisional application of U.S. Ser. No. 834,199, filed Feb. 27, 1986, and now granted as U.S. Pat. No. 4,700,716.

BACKGROUND OF THE INVENTION

I. Field of the Invention

The present invention relates in general to microwave balloon angioplasty, and pertains more particularly to a microwave or radiofrequency catheter system for the heating of plaque in arteries or blood vessels. Also described herein are improvements pertaining to features of the microwave catheter system, including improved antenna constructions and associated fiberoptics.

II. Background Discussion

Balloon angioplasty is now a relatively well-accepted alternative to bypass surgery for high-grade obstructive atherosclerotic lesions of the peripheral, renal and coronary vessels. In this regard, U.S. Pat. No. 4,643,186, entitled "Percutaneous Transluminal Microwave Catheter Angioplasty," by Rosen et al., describes a coaxial cable and antenna for microwave heating of artery plaque. This system suffers from several shortcomings which make it difficult, if not impossible, to develop a well controlled volume of heat within the plaque material. Also, for small arteries where catheter diameter and flexibility are critical, the system described by Rosen et al. does not allow for sufficient transmission of microwave power to the plaque for welding purposes. Recent work with laser balloon angioplasty demonstrates the need to heat the plaque to nominally 100° C. for 30 seconds. For a 1.34 m. length of commercial microwave coax, the insertion loss at 10GHz is approximately 10 dB. This frequency corresponds to a depth of penetration in plaque of 3 mm. Therefore, a 35 watt load requirement for heating plaque to nominally 100° C. requires a 350 watt power supply (RF). This situation is not practical. The transmission line itself would heat up, because 315 watts is dissipated by it during power transmission to the plaque (load). The monopole antenna described in Rosen et al. does not provide radiation confined solely to the distal end inside the balloon. A very nonuniform radiation pattern is developed with antenna current leaking back up the outside surface of the outer conductor, which forms the coax. The resulting heating pattern is sharply peaked at the point along the coax where the inner conductor protrudes outside of the outer conductor and a secondary heating pattern develops along the length of the coax back to the generator. Leakage currents produce the secondary heating pattern. This may result in melting of the catheter plastic material.

Accordingly, it is an object of the present invention to provide an improved technique for the heating of plaque in arteries, veins or blood vessels, such as in association with microwave balloon angioplasty.

Summary of the Invention

To accomplish the foregoing and other objects, features and advantages of the invention, there is provided a microwave or RF catheter system for heating arterial plaque. In accordance with one embodiment of the present invention, there is provided a flexible catheter member adapted for positioning in the artery and adapted to support at the distal end thereof an inflatable balloon. A microwave signal generator is disposed at the proximal end of the catheter member. A transmission line means couples from the signal generator through the catheter member and includes at its distal end an antenna means. Optic fiber means extends through the catheter member between proximal and distal ends thereof, and has one end thereof disposed in the balloon in juxtaposition with the antenna means. Channel means extend through the catheter member between proximal and distal ends thereof for coupling a fluid to the balloon for inflation thereof.

In accordance with further features of the present invention, the channel means has an entrance port to the balloon and further includes a pressurized fluid source for introducing fluid to the balloon under pressure. The signal generator is excited for a predetermined period of time upon injection of the inflating fluid. The optic fiber means has a sensor at the distal end within the balloon to measure temperature in or at the surface of the balloon, and in one embodiment, a pair of sensors are employed for measuring temperature at separate locations within the balloon. The antenna means may comprise a collinear array antenna. This antenna may be disposed inside of the balloon, or may be disposed within the skin forming the balloon. The collinear array antenna may be formed in a spiral to provide full balloon circumferential coverage, or may, alternatively, be formed in a helix. In still a further embodiment of the invention, the collinear array antenna may include separate antenna sections in combination with a power divider for intercoupling the transmission line to the separate antenna section. The separate antenna sections may be disposed in opposite locations in the balloon. In still another embodiment of the invention, the antenna means may comprise a plurality of separate collinear array antennae. There may also be provided separate transmission lines in the catheter member for each of the collinear and array antennae. In a further embodiment of the invention, the antenna means may comprise a microstrip radiator. The microstrip radiator may be comprised of a conductive strip and a ground plane, separated by a dielectric substrate. The radiator may be of annular configuration, having an outer radiating strip. In one embodiment, the radiator includes a hollow member coated with a conductive film to form a ground plane, a thin dielectric film over the ground plane and a conductive antenna pattern printed over the dielectric film surface. The antenna pattern may be in a spiral or helix configuration.

In accordance with still further embodiments of the present invention, the transmission line may be in the form of a stiff guide member that retains sufficient stiffness and yet is flexible. In this embodiment, there is provided a guide wire forming a center conductor. Impedance matching means are provided along the center conductor at locations where the center conductor enters and leaves the balloon. The transmission line has an outer conductor except at positions within the balloon and the tip of the center conductor extends beyond the balloon in this embodiment. In still another embodiment of the present invention, there may be provided a plurality of metallic filaments, each having a length of one-half wavelength or less at the microwave frequency of operation. An active antenna within the balloon is used for exciting these filaments. The filaments may be disposed either inside the balloon or within the skin of the balloon. In another embodiment of the invention, the antenna means is comprised of a plurality of spacedly disposed antenna wires arranged about the balloon near the inside surface thereof, and commonly coupled to the transmission line.

In accordance with still a further feature of the present invention, there is provided a triaxial fiberoptic/RF cable that is in the form of a fiber core having multiply deposited layers on the core, including a conductive layer defining a conductor, a dielectric coating defining an insulating layer and an outer conductive layer defining an outer conductor.

In accordance with still a further embodiment of the present invention, the balloon itself is constructed of a compliant material that is either loaded with a lossy material or coated with a flexible material sufficiently loaded with lossy particles to allow for absorption of microwave energy in the balloon directly. Also, the fluid within the balloon may be of a type having lossy particles in suspension. The lossy material used may include ferrite or graphite materials.

BRIEF DESCRIPTION OF THE DRAWINGS

Numerous other objects and advantages of the invention should now become apparent upon a reading of the following detailed description, taken in conjuction with the following drawings, in which:

FIG. 20 is a cross-sectional view of the antenna of the antenna construction of the present invention showing, in solid lines, a cross-section of one-half of the far field antenna array pattern, each of the three antenna elements, and in dotted lines the near field heating pattern resulting from the superposition of the electromagnetic energy pattern generated by the three antenna elements;

FIG. 21 is a cross-sectional view of the antenna of FIG. 1 along the lines 21—21;

FIG. 22 is a cross-sectional view of the antenna of FIG 20 along the lines 22—22;

FIG. 23 is a cross-sectional view of the antenna of FIG. 20 along the lines 23—23;

FIG. 24 is a cross-sectional view of the antenna of FIG. 20 along the lines 24—24;

FIG. 28 is a cross-sectional view of an alternate embodiment of the outermost end of the antenna construction;

FIG. 29 is an enlarged fragmentary view of FIG. 28; and

FIG. 30 is a cross-sectional exploded view of a flexible coaxial connector adaptor system for use with the antenna of FIG. 20 as shown in the process of being assembled;

FIG. 31 schematically illustrates a four wire transmission line antenna system;

FIG. 32 illustrates a five wire transmission line antenna system;

FIG. 33 illustrates helix radiation patterns;

DETAILED DESCRIPTION

Figure 1:
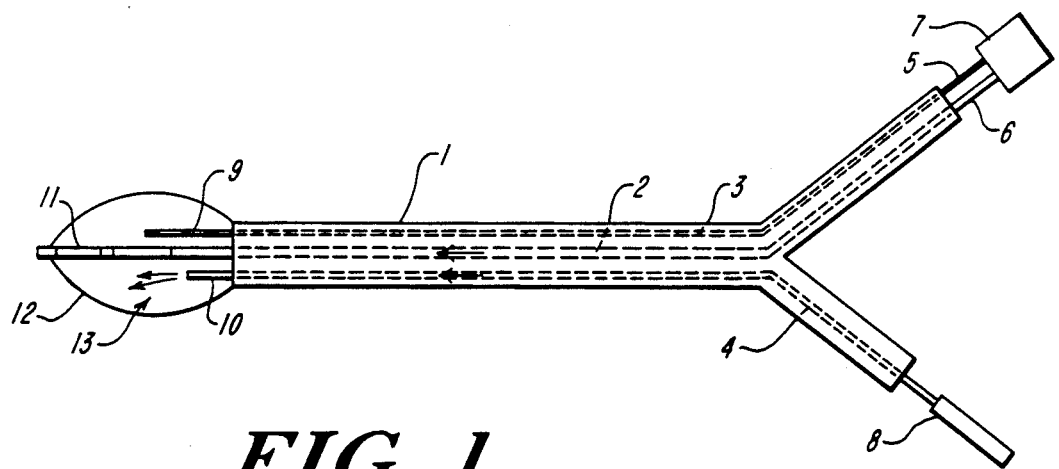
FIG. 1 is a diagram of one embodiment of the present invention, employing a microwave balloon catheter with a fiberoptic temperature sensor.

Reference is now made to the drawings herein that illustrate a number of different embodiments of the present invention. The concepts of the present invention are explained herein in association with a microwave balloon angioplasty technique. However, the concepts of the present invention may also be used with energy in frequencies of the electromagnetic spectrum outside of the microwave range. Also, the concepts of the present invention may be employed in higher temperature ranges, such as for ablation purposes.

It is desired to supply microwave heat to the plaque material only in microwave balloon angioplasty. In this connection, experimental work with laser balloon angioplasty has demonstrated that welding of the plaque from heat and pressure results in reduced restenosis. Microwave energy, when delivered to the plaque in a sufficient amount, likewise is helpful in preventing restenosis by application of heat and pressure. Laser energy absorption in plaque for melting may be the result of interaction with the water molecules' vibration energy levels, whereas microwave energy absorption in plaque may be the result of interaction with the water molecules' dipole moment or rotation energy levels.

In accordance with the present invention for successful delivery of microwave energy to the plaque, a highly flexible miniature transmission line is used, that can transmit sufficient radiofrequency or microwave power to the load (plaque). This transmission line is to be kink-free, because of the requirement of relatively small turning radii.

In accordance with the present invention, the antenna system is to be designed to deliver microwave energy to a specific layer of plaque without heating wall tissue during pressure application by the balloon. The liquid that inflates the balloon preferably does not absorb any substantial microwave energy. It is instead preferred that the energy be concentrated at the plaque rather than in the liquid itself that causes the balloon's expansion.

In connection with certain fabrication techniques for the highly flexible miniature transmission line, reference is made to description set forth hereinafter relating to FIGS. 20-30.

In accordance with the present invention, there are now described a number of techniques for providing control of the quantity of microwave energy that is coupled to coronary vessel plaque without heating vessel tissue. A collinear antenna array is provided inside the balloon or between two balloon surfaces (balloon inside a balloon). In accordance with one embodiment of the invention, a printed microstrip circuit radiator or antenna pattern is configured in one of several ways, such as inside the balloon, between balloon surfaces or outside the balloon.

In accordance with another embodiment of the invention, the antenna may be formed from a guide wire. In another embodiment of the invention, a collinear array antenna configuration may be provided inside the balloon and the balloon may be fabricated with either a magnetic or dielectric lossy coating on its surface or the balloon itself may be loaded with a similar lossy material so as to provide direct balloon heating.

In accordance with another embodiment of the invention, to be described in further detail hereinafter, there is provided an array of resonant thin wire dipoles over the entire balloon surface or embedded within the balloon material. These dipoles may be parasitic elements driven by an active antenna.

In still a further embodiment of the present invention described hereinafter, a wire balloon monopole is provided. A group of thin parallel wires is connected at one end to the feed coax and forms an expanded center conductor. Each wire lies on the surface or inside the balloon material.

All of the above mentioned embodiments will be described hereinafter in further detail. These various embodiments may be employed to precisely deliver microwave or radiofrequency energy to plaque during a pressure treatment. An alternate heating approach involves much higher temperatures than 100° C. (for example, 400° C.-500° C.), and involves an embodiment in which the microwave antenna axis of the collinear array is extended beyond the end of the balloon. In this regard, refer to FIG. 14 herein. Also refer to FIG. 27 that illustrates the employment of a ferrite sleeve 80 associated with the antenna.

Figure 14:
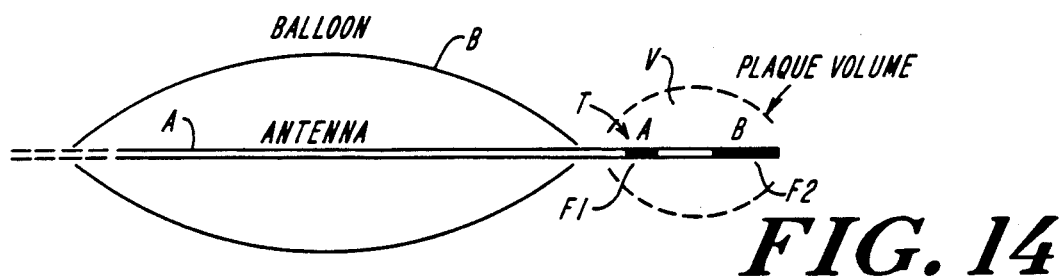
FIG. 14 schematically illustrates the use of a pair of ferrite sleeves disposed a distance apart along an antenna axis but outside of the balloon.

FIG. 14 shows the antenna A extending through the balloon B and having at its tip T a concentric layer of ferrite material that may have a Curie temperature in the 400° C.-500° C. range. Microwave energy is rapidly absorbed in the ferrite when this material is at a current maximum of the antenna. The primary function of this hot tip (when the ferrite is at the far end of the antenna) is to melt plaque (ablation). This is used for those cases where the artery is fully blocked by plaque, and it would therefore be necessary to remove some plaque in order to insert the balloon. In FIG. 14, note the plaque volume at V. Once some plaque has been removed, the balloon may be inflated and the microwave angioplasty carried out.

Figure 27:
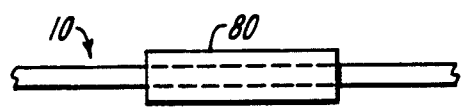
FIG. 27 is a side view of an optional embodiment of the invention employing a lossy sleeve.

As indicated previously, FIG. 27 herein teaches the use of a lossy sleeve 80 for focused heating. An alternate embodiment is to employ two ferrite sleeves F1 and F2, as illustrated in FIG. 14, some distance apart along the antenna axis but outside of and essentially in front of the balloon. In this regard, the arrow A1 in FIG. 14 illustrates the direction of insertion of the antenna structure.

As indicated previously, FIG. 14 shows a two-ferrite geometry. The ferrites F1 and F2 heat through the plaque (occluded artery) using microwave frequency F1. To withdraw the antenna back through the plaque and avoid sticking, the ferrite F2 is tuned to a frequency F2. It remains hot to allow the antenna to be withdrawn prior to inserting the balloon and using the antenna in its normal temperature plaque welding mode. Also, this ferrite, hot tip antenna may be completely removed from the catheter in a different antenna design employed for low temperature operation.

Figure 2:
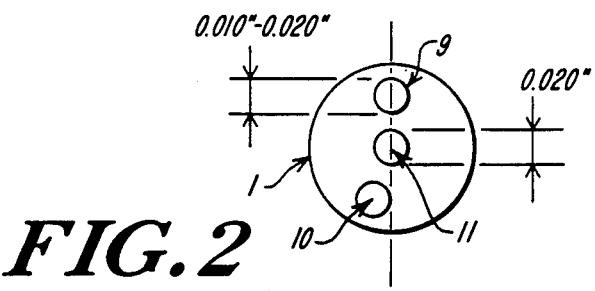
FIG. 2 is a cross-sectional view at the balloon end of the apparatus.

Reference is now made to one embodiment of the present invention illustrated in FIGS. 1 and 2 herein. This employs a collinear antenna array that may be of the type to be described in further detail herein in FIGS. 20-24. This arrangement provides localized microwave heating energy to provide a circumferential heat treatment during balloon angioplasty for the purpose of sealing, preventing abrupt reclosure, and preventing restenosis in patients with vascular disease.

As indicated previously, one embodiment of a collinear array antenna is described in further detail hereinafter in FIGS. 20-24. The collinear array antenna is positioned inside the balloon and preferably as near to the balloon's surface as is practical. The balloon is inflated with a low dielectric loss fluid that may be a liquid or gas. A low loss dielectric material is preferred so as to minimize microwave energy coupling to the fluid. Several different embodiments will be described hereinafter in, for example, FIGS. 1-13.

In accordance with the present invention, it has been found that the use of microwave energy is considerably less expensive than a laser probe with its associated driver. In accordance with the invention, heat is also controlled by a fiberoptic sensor in close proximity to the antenna for providing accurate temperature readings during microwave power application. This ensures precise temperature control to avoid excessive heating. The outer diameter of the coaxial cable is preferably 0.02". This allows easy placement of the cable in a standard balloon catheter. Alternatively, in accordance with the invention, the antenna may be used in combination with a ferromagnetic sleeve in the ablative mode to eliminate plaque buildup. The ferrite sleeve permits high localized temperatures to be generated by microwave energy absorption within the sleeve volume. Further embodiments of the invention cover this feature, such as will be illustrated and described in further detail herein in FIGS. 18 and 19.

Reference is now made to one embodiment of the present invention illustrated in FIGS. 1 and 2. This embodiment illustrates the microwave balloon catheter 1 with a fiberoptic temperature sensor. A cross-section schematic of the balloon end is illustrated in FIG. 2. The balloon 12, it is noted, is secured to the distal end of the catheter member 1. The catheter member 1 has three lumens for carrying, respectively, the microwave coaxial transmission line 2, the fiberoptic cable 3, and the channel 4, which is for the coupling of the electrically low loss fluid 13 to the balloon 12 for inflation purposes.

FIG. 1 also illustrates, in the system, a microwave signal generator 7 that includes fiberoptic temperature processing circuitry. The generator 7, it is noted, couples with the cable 6 and also the fiberoptic cable 5. These cables are continuations of the aforementioned cables 2 and 3.

FIG. 1 also illustrates the fluid source 8, which may comprise a pump for pressurizing the fluid, connected to the channel 4. As indicated previously, the fluid 13 pumped from the source 8 is preferably a low loss tangent liquid or gas that is adapted to minimize microwave or radiofrequency energy absorption.

The balloon 12 is inflated by means of the liquid 13 injected into it under pressure at the entrance port 10. FIGS 1 and 2 also illustrate a microwave antenna 11 that supplies electromagnetic energy to the liquid 13 for, say, a period of 30 seconds. The liquid 13 is low loss so that the energy from the antenna is concentrated outside the balloon skin rather than in the liquid itself.

The antenna 11 is adapted to provide an axially uniform power pattern along its active length, which is contained within the balloon. The antenna construction is such that no microwave power leaks back along the feed cable 2. It is preferred to employ a collinear array antenna as described in further detail hereinafter in FIGS. 20-24.

FIGS. 1 and 2 also show the temperature sensor 9 within the balloon 12. Instantaneous temperature rise is measured by the sensor 9, preferably at two points within the balloon. The fiberoptic sensor is coupled to a fiberoptic transmission line that may have a diameter of 0.01" for a single temperature measurement point or may be 0.02" for simultaneous two-point temperature measurement. A typical balloon length and diameter are 2 cm and 3 mm, respectively, for coronary artery angioplasty. The antenna may be coated with a lossy magnetic material to provide temperatures in the range of 450° C.-500° C. for ablation purposes. In such an application, the antenna is employed before balloon angioplasty.

Further embodiments of the collinear array antenna are now described in FIGS. 2-6. In these embodiments it is desired to provide an omnidirectional and uniform heating pattern and, thus, the antenna may be wound in helical or spiral fashion, so that its radiation pattern provides a full 360° of balloon circumference.

The frequency of operation and, therefore, the antenna-design parameters, are controlled by the desired depth of penetration of microwave energy into the plaque. At a 3 mm depth of penetration, the frequency is nominally 10 GHz, with a 1.5 cm antenna length. The balloon length and length of the plaque deposit should coincide with the antenna length, as measured along the balloon axis. Alternatively, the collinear array may be positioned along the axis of the balloon and inside the balloon, as depicted previously in FIG. 1.

Figure 3:
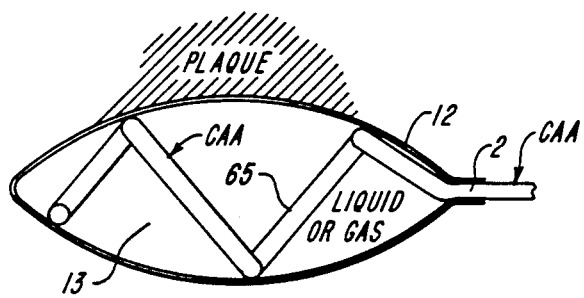
FIG. 3 illustrates a spiral configuration of the collinear array antenna.
Figure 4:
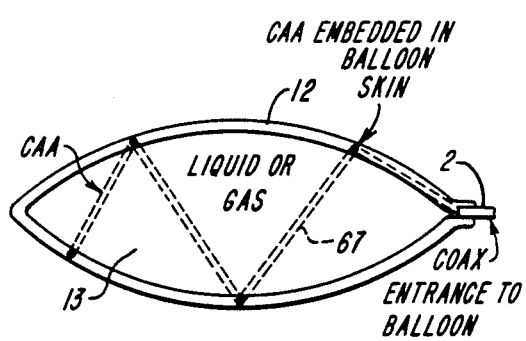
FIG. 4 illustrates a spiral configuration of the collinear array antenna embedded inside the skin of the balloon.

A reference is now made to FIGS. 3-6 for further embodiments of the antenna construction. FIG. 3 illustrates the collinear array antenna 65 coupled from the coaxial transmission line 2. The antenna 65 is provided in a spiral or helical configuration. In this embodiment of the invention, it is noted that the antenna is disposed substantially exclusively inside the balloon. However, in the alternate embodiment of FIG. 4, it is noted that the spiral or helical configuration of the collinear array antenna is embedded in the balloon skin.

Figure 5:
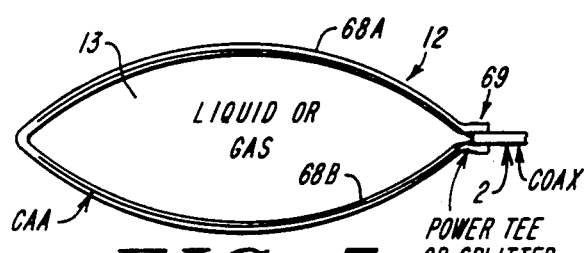
FIG. 5 illustrates two collinear array antennae in the balloon skin and fed by a power tee or power splitter.

Reference is now made to FIG. 5 for still a further embodiment of the present invention. This embodiment employs two separate collinear array antennae 68A and 68B embedded in opposite sections of the balloon skin. These antennae are fed from the coaxial line 2 by means of a power tee or power splitter, illustrated at 69 in FIG. 5.

Figure 6:
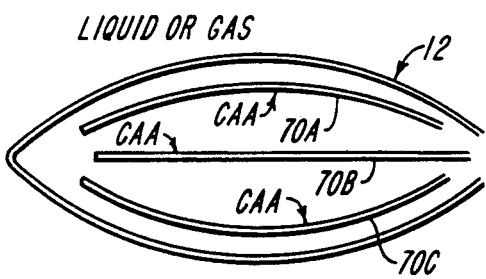
FIG. 6 illustrates separate collinear array antennae, each fed from a separate transmission line.

Reference is now made to FIG. 6 for a further embodiment of the present invention employing three separate collinear array antennae 70A, 70B and 70C. In this embodiment, each of these antennae is provided inside the balloon skin, as illustrated. Each of these antennae may couple to its own separate coaxial microwave transmission line. For this purpose, the catheter member, such as member 1, illustrated in FIG. 1, may be provided with means for accepting each of these separate transmission lines. In all embodiments of FIGS. 2-6, a fluid 13 is contained in the balloon and is used for the purpose of inflating the balloon. This fluid is preferably a low loss fluid as indicated previously.

Figure 7:
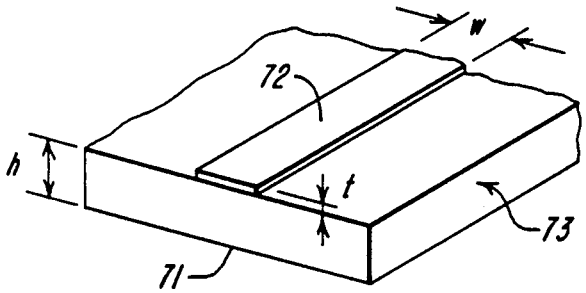
FIG. 7 illustrates a microstrip geometry in accordance with the present invention.
Figure 8:
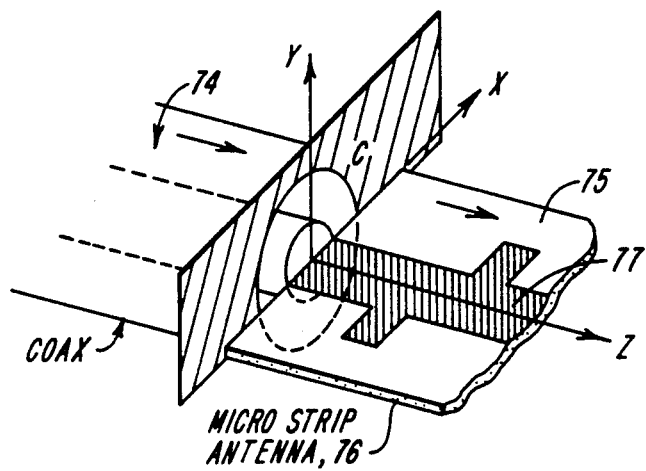
FIG. 8 is a perspective view illustrating an alternate embodiment of a microstrip antenna.

Reference is now made to FIGS. 7-10 for various microstrip printed antenna constructions. Microstrip is a type of open wave guiding structure that is a simple construction and can be fabricated readily in miniature size. The microstrip antenna, such as that illustrated in FIGS. 7 and 8 herein, is manufactured using printed circuit board techniques. In this connection, a relatively simple patch radiator is shown in FIG. 7. A somewhat different configuration is illustrated in FIG. 8.

In FIG. 7, the microstrip geometry includes a dielectric substrate 73 that has supported on its upper surface a printed conductive strip 72 of metal which is suitably contoured. The lower surface of the dielectric substrate 73 is backed by a conducting metal forming a ground plane 71. The microstrip patch radiator illustrated in FIG. 7 can be used in various applications where a flat radiator is appropriate. Such a conformal design is suitable for microwave balloon angioplasty.

FIG. 8 shows a slightly different version of the microstrip antenna, employing an antenna 77 supported on a dielectric substrate 75 and also illustrated in a ground plane 76. It is noted that the antenna 77 is fed from the center conductor of coax 74. In this connection, the dielectric substrate is preferably a low loss substrate such as titanium dioxide.

Figure 9:
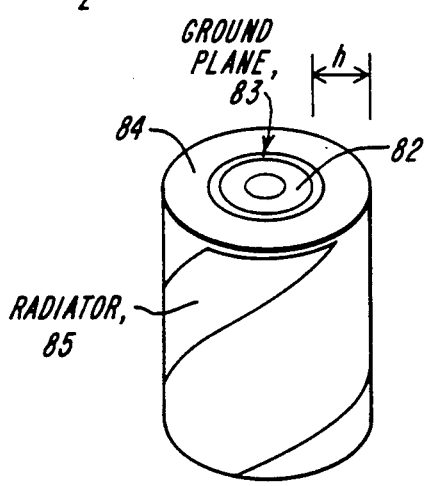
FIG. 9 illustrates a microstrip spiral radiator adapted to be placed in a balloon.

Reference is now made to FIG. 9 for a practical application of a microstrip geometry to microwave balloon angioplasty. The microstrip spiral radiator of FIG. 9 is adapted to be placed in a balloon with the long axis of the balloon parallel to the long axis of the spiral radiator. The overall antenna structure of FIG. 9 may be comprised of a cylindrical core 82. This core 82 may be of a rubberlike material, and may be hollow, so as to accept an optical fiber. The surface of the core 82 may be coated with a thin film of highly conductive metal to provide a ground plane, as indicated at 83 in FIG. 9. Next, a thin dielectric coating or film is provided over the entire ground plane surface. This is illustrated at 84 in FIG. 9. The dielectric coating may be, for example, titanium dioxide. A conductive antenna pattern is printed, as illustrated at 85 in FIG. 9, over the dielectric film surface. The pattern 85 may be provided in a continuous spiral patch, as illustrated in FIG. 9, or, alternatively, a wraparound radiator may be provided as illustrated at 87 in FIG. 10.

Figure 10:
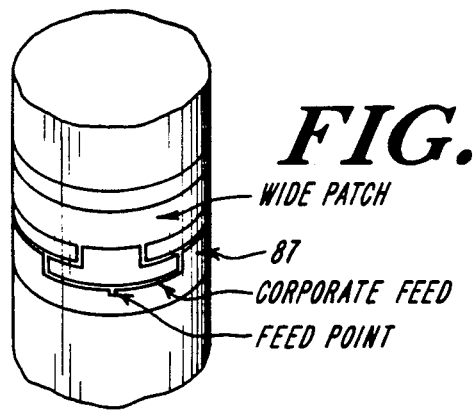
FIG. 10 illustrates a microstrip wrap-around radiator in accordance with the present invention.

In the embodiment of FIG. 9, the coaxial transmission line that feeds microwave or radiofrequency energy to the printed radiator pattern may be connected at one end of the radiator. The cylindrical geometry is well suited for the application of balloon angioplasty. However, a simple version for heating plaque may employ a flat antenna geometry as illustrated in FIG. 8. In FIG. 10 the ground plane may be curved to match the balloon curvature lengthwise or remain straight and parallel to the balloon axis.

Figure 11:
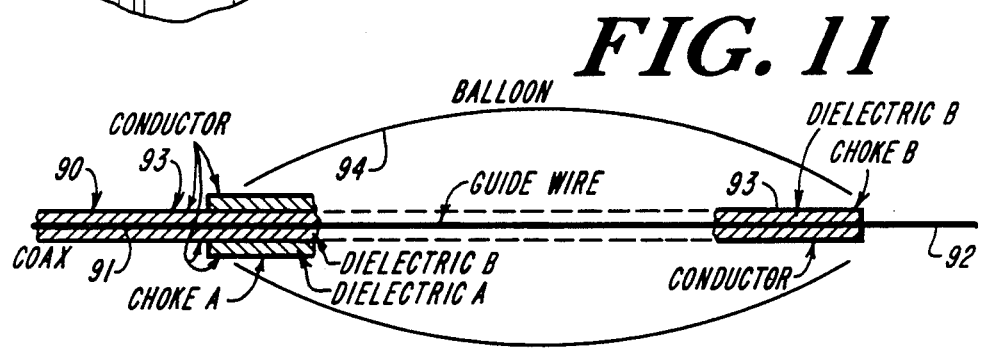
FIG. 11 illustrates a guidewire antenna system in accordance with the present invention.

Reference is now made to FIG. 11 for still another embodiment of the present invention in the form of a guide wire antenna system. The guide wire essentially provides some stiffness to the catheter and makes it easier to guide the catheter along the artery channel. The guide wire itself may be employed to form the center conductor of a feed coaxial transmission line. In this regard, in FIG. 11, note the coaxial line 90 and the guide wire 91, which furthermore extends through the balloon to the tip 92.

As indicated previously, the guide wire is used as the center conductor of the flexible coax 90. It is coated with a dielectric and then a metallic film outer conductor, as illustrated at 93, except for the region within the balloon 94, and, furthermore, except for the area at the tip 92.

In the embodiment of FIG. 11 chokes A and B are formed. These chokes may also be referred to as impedance matching transformers, and may be of the type to be described hereinafter in association with FIG. 20. The chokes A and B are formed where the guide wire 91 enters and leaves the balloon 94 to prevent antenna currents from forming between the choke B and the tip 92 and the choke A and the transmitting end (current along the outer surface of the conductor). The guide wire 91, with or without a dielectric coating, along its length between chokes A and B, is the radiation portion of the system.

Figure 12:
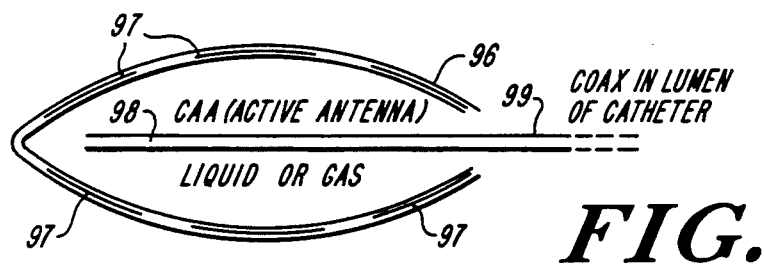
FIG. 12 illustrates a further antenna arrangement employing an active antenna and associated parasitic array elements.

Reference is now made to FIG. 12 for a further embodiment of the present invention, employing parasitic array elements embedded in the balloon skin. In particular, in FIG. 12, there is illustrated the balloon 96, having embedded therein a two-dimensional array of metallic filaments or wires 97. Each of these filaments or wires may be one-half wavelength along or less at the microwave frequency of operation. The filaments are embedded in the skin of the balloon, or, alternatively, may be located inside the balloon. FIG. 12 also shows an active antenna element at 98 coupled to the coax line 99. The filaments or wires 97 are excited by the active antenna 98, which is relatively closely coupled to the elements 97. The elements 97 in turn radiate microwave energy into the plaque.

Figure 13:
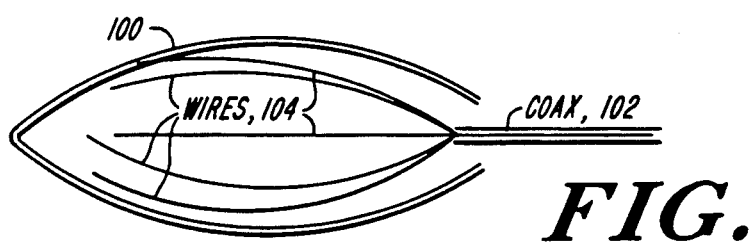
FIG. 13 illustrates a further embodiment of the invention employing plural separate antenna wires fed from a common coax.

Reference is now made to FIG. 13 for still a further embodiment of the present invention. FIG. 13 illustrates the balloon 100 as connected to a group of thin wire filaments 104 that are disposed at or near the inner balloon surface. This grouping of filaments or wires provides a substantially expanded center conductor for radiation directly into the plaque. In the embodiment of FIG. 13, the filaments 104 may be disposed in a fanned-out arrangement about substantially the full circumference of the balloon.

The conventional balloon construction employed in balloon angioplasty is normally manufactured using a clear, low microwave loss plastic material. However, in accordance with the present invention, there is now proposed a technique of heating plastic with microwave energy when the balloon surface is in intimate contact with the plaque. This technique of the present invention is characterized by a balloon loaded with a lossy ferrite or graphite material, such as a ferrite or graphite powder, that permits the balloon material to absorb microwave energy and therefore heat up. Alternatively, a similar lossy coating may be employed on the balloon surface to absorb microwave energy. The energy is provided by a microwave antenna located inside the balloon. The coated (or both coated and loaded) balloon serves two important functions. Heat may be directly applied to the surface of the plaque without the microwaves depending on the plaque material to have sufficient electrical loss (loss tangent) for heat-up, and the balloon may act as an attenuator of microwave energy to control the amount of microwave energy radiated directly into the plaque. In this particular mode of operation, the balloon is not necessarily being counted on to provide interface heating.

Figure 15:
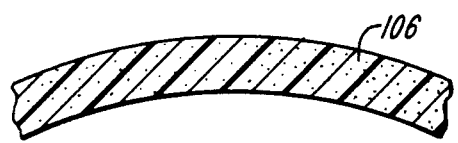
FIG. 15 is a fragmentary view illustrating a balloon skin with lossy loading.
Figure 16:
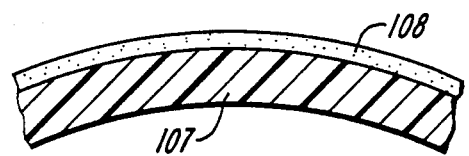
FIG. 16 is a fragmentary view of a balloon skin with an external lossy coating.
Figure 17:
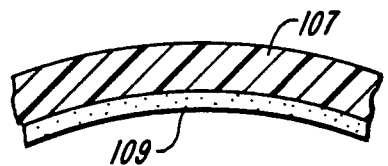
FIG. 17 is a fragmentary view of a balloon skin with an internal lossy coating.

With respect to this technique of balloon skin loading, reference is now made to FIGS. 15-17. FIG. 15 schematically illustrates at 106 the balloon skin itself, loaded with a lossy material such as a ferrite or graphite powder. FIG. 16 shows the balloon skin 107 with an external coating 108. FIG. 17 shows the balloon skin 107 with an internal coating 109. The coating may be of a flexible paintlike material sufficiently loaded with lossy particles. Alternatively, in still another embodiment of the invention, the balloon may be inflated with a viscous fluid holding lossy particles in suspension. As illustrated in FIGS. 16 and 17, the coating may be applied either on the inside or outside surfaces of the balloon and, furthermore, combinations of the embodiments described may be employed.

Figure 18:
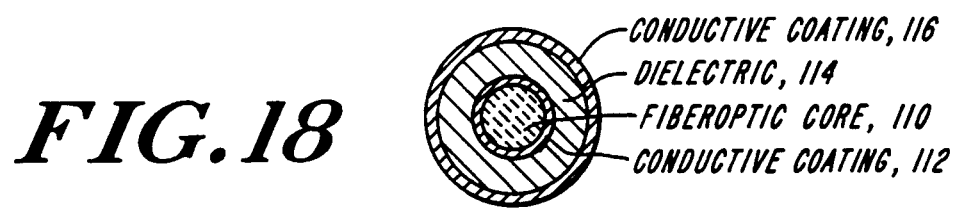
FIG. 18 illustrates the triaxial fiberoptic/RF cable as in accordance with the present invention adapted to transmit RF energy to a ferrite sleeve.
Figure 19:
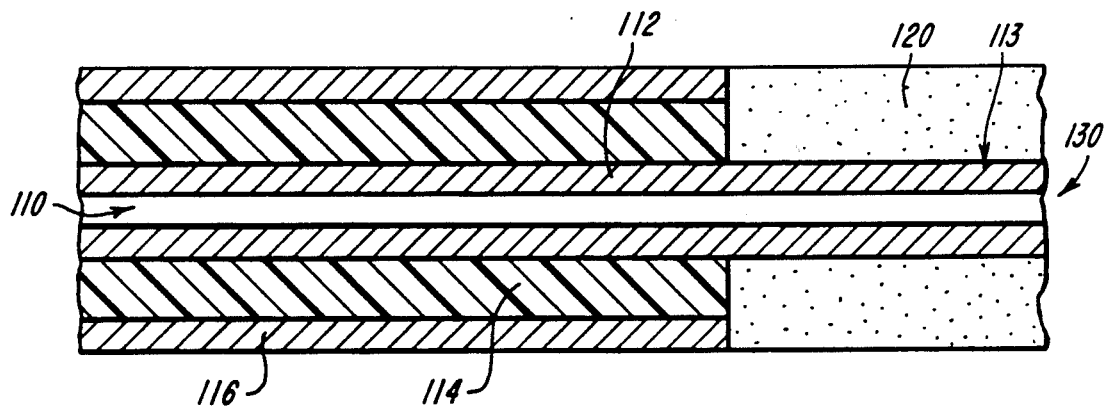
FIG. 19 is a further view of the embodiment of FIG. 18 showing further details.

With reference to various embodiments of the invention described hereinbefore, it is to be noted that balloon angioplasty and associated ablation techniques may be carried out with a triaxial applicator geometry, such as that illustrated in FIGS. 18 and 19 herein. This arrangement provides for an integral microwave or radiofrequency transmission line in combination with a fiberoptic core for temperature sensing or for other purposes. This arrangement is also preferably used in association with a ferrite sleeve.

The triaxial fiberoptic/RF cable may be used either as a cable to transmit microwave energy to a ferrite sleeve for heating purposes, or as an applicator for microwave application for medical, scientific, or industrial purposes that would also have an optical capability. This optical capability could be used for several purposes, i.e., visual observations, temperature sensing, lasing, etc.

The basic triaxial applicator is illustrated in FIG. 18 and is comprised of a fiberoptic cable 110, which is the heart of the system. For the particular application to microwave balloon angioplasty, the fiberoptic cable is used for temperature sensing purposes. A conductive coating, illustrated in FIG. 18 by the coating 112, is applied to the fiberoptic cable. This coating becomes the microwave carrying portion of the microwave-/fiberoptic system.

A fiberoptic coating 114 is then applied to the conductive coating. The dielectric layer 114 is of proper dielectric value and thickness to make the cable a preferred 50 ohm transmission line. Another conductive coating 116 is applied to the dielectric layer to form the outer conductive shield of the cable. Reference is also now made to the cross-sectional view of FIG. 19 that furthermore shows the system as employed with a ferrite sleeve 120. The antenna system, including in particular the inner conductor 112 at its tip 113, may accommodate the ferrite sleeve 120. This device converts microwave energy to thermal heat in the ferrite sleeve. The fiber core may be used for the purpose of temperature sensing in association with a feedback system for control of the temperature of the ferrite sleeve. It may also find other applications in medicine, such as for cauterizing. The embodiment disclosed in FIG. 19, in particular, is used to melt or heat plaque in arteries.

Reference is now made to FIGS. 20–24 for an illustration of a microwave collinear array antenna in the form of an applicator 10 for uniform heating of a substance such as a tumor, or, in the embodiments described herein, the heating of plaque in an artery. This heating is performed within well-defined temperatures. The antenna structure is shown in the form of a collinear array of three antennae fabricated from a coaxial transmission line comprising inner conductor 20 and outer coaxial conductor 16, with an impedance matching element 26.

The three antennae are formed by providing circumferential gaps 5 in the outer conductor 16 to expose the dielectric core 18 of the transmission line structure. Preferably, the widths of the gaps 5 are about the same size as the distance between center conductor 20 and outer conductor 16. Core 18 may comprise a suitable solid dielectric insulator, such as PTF (polytetrafluoroethylene). The gaps 5 provide excitation feeds for more remote, i.e., more distal end, antenna sections and result in the equivalent of more than one antenna pattern being generated from the length of the center conductor. The electrical lengths of these antenna sections are harmonically related to each other.

A dielectric outer envelope 14, containing fiber optic sensors 24, extends over the outer surface of the applicator 10. For antenna beam steering purposes, a resistor 22 is provided at the longitudinal axis of the applicator. In accordance with the theoretical and experimental teaching of Altschuler ("The Traveling-Wave Linear Antenna," E. E. Altschuler, Cruft Laboratory, Harvard University, Cambridge, Mass., *Scientific Report No. 7*, May 5, 1960), an essentially traveling-wave distribution of current can be produced on a linear antenna by inserting a resistance of suitable magnitude one-quarter wavelength from the end of the antenna. As shown in FIG. 21 from the above-cited reference, the effect of such resistance is to significantly change the radiation pattern of the antenna and therefore, in the present application, its heating pattern for hyperthermia. The collinear array applicator 10 of the present invention is therefore provided with the appropriate value of resistance about one-quarter wavelength from the end of the distal section. By changing the applied frequency, or the location of the resistor, the distribution of heat around the applicator may therefore be changed or "steered" in many directions At the proximal end of the antenna array 10, a coaxial impedance matching transformer is provided, in the form of a dielectric cylinder 26 concentric with and external to the outer conductor 16. The dielectric cylinder 26 is covered with a metallic cylinder 27, which is electrically shorted to outer conductor 16 at proximal end A. A dielectric outer envelope 14 extends over the full length of cylinder 27 and distal section B-E. The transformer minimizes the reflected power within the feed transmission line and also prevents leakage of antenna currents along the outside of the array applicator 10. By judicious selection of operating parameters, both functions (minimizing reflected power and leakage prevention) occur at approximately the same operating frequency. The operating parameters of the coaxial impedance matching transformer are based on the theoretical equations developed by R. W. P. King, ("The Electromagnetic Field of an Insulated Antenna in a Conducting or Dielectric Medium," R. W. P. King et al., *IEEE Transactions on Microwave Theory and Techniques*, Vol. MIT-31, No. 7, July 1983).

The transformer provides a load impedance at the proximal end of the collinear arrays for RF power coupled from source 12 via lines 30 and 32 across the inner and outer conductors 20 and 16. This load impedance regulates the antenna current at the feed points or gaps 5 to more nearly match the 50 ohm impedance of the feed transmission line 30 and 32 with the input impedances of the collinear array 10. The distal section of applicator 10 of FIG. 20 has an overall length B-E of 10 cm at a frequency of 915 megahertz. This length is a multiple of one-half of the wavelength of the input frequency, (i.e., 5, $\lambda_L/2$ sections) and is physically represented by a full-wave linear antenna (C-E) series connected to a three-halves wave linear antenna (B-C). This arrangement of antennae provides a uniform heating pattern shown in the dotted lines labelled B4 of FIG. 20).

Note that heating pattern B4 is one-half of a plane cut through the full cylindrical near field heating pattern extending from array 10, which is related to the superposition of the three individual far field antenna patterns B1, B2 and B3, shown in solid lines. If a shorter antenna array is desired, the frequency may be doubled and the length halved. Alternatively, for the same frequency, section C-D can be removed to reduce the length to 8 cm or section B C can be removed to reduce the length to 4 cm.

In operation, as the transmitted power from source 12 flows down the coaxial line formed by inner and outer conductors 20 and 16, separated by dielectric 18, voltage excites each antenna section and electromagnetic energy is radiated from the applicator and absorbed by the lossy tissue. The absorbed energy reduces the amplitude of the transmitted power. By increasing the number of elements at the distal end of the array (and decreasing the spacing between elements), a higher sectional antenna gain is achieved, as compared to the more proximal section B-C, which will have a lower gain because it is a single ($3\lambda/2$) element.

More specifically, the square of the electric field for the half-wavelength [1], full wavelength linear [2] and 3/2 wavelength [3] antennae in free space, shown below, provides an indication of the radiated power distribution for the collinear array in lossy material (J. D. Jackson, "Classical Electrodynamics," J. Wiley, 1975, 2nd ed , pp 402–403):

$$\text{For } \frac{\lambda}{2} \text{ Antenna: } E^2 \alpha \frac{\cos^2 (2 \cos\theta)}{\sin^2 \theta} \quad (1)$$

$$\text{For } \lambda \text{ Antenna: } E^2 \alpha \frac{4 \cos^4 \left(\frac{\pi}{2 \cos\theta}\right)}{\sin^2 \theta} \quad (2)$$

$$\text{For } \frac{3\lambda}{2} \text{ Antenna: } E^2 \alpha \frac{\cos^2 (3\pi/2 \cos\theta)}{\sin^2 \theta} \quad (3)$$

wherein $\theta$ is measured from the longitudinal axis of the antenna.

The full wave antenna, distribution (C-E), can be considered as resulting from the coherent superposition of the fields of two collinearly adjacent half-wave antennae patterns $B_2$ and $B_3$ excited in phase; the power intensity at $\theta = \pi/2$ is 4 times that of half-wave length antenna. Thus, the extreme distal section (C-E) of two series connected half wave antennae radiates 6 dB more power per solid angle than the three half wave length section (B-C). Based on geometric reasoning, the total power radiated by the three half wave length antenna is about 60% of the total power delivered to the array (6 cm length compared with 4 cm length). Therefore, forty percent is left over for radiation by the series connected half wave antennae (C-F). The 6 dB gain of the $3\lambda/2$ section compensates for this loss. The result is a nearly uniform heating pattern along the entire 10 cm length of distal section B-E of array applicator 10.

Preferably, the collinear array applicator 10 is fabricated using standard AWG (American Wire Gauge) solid or stranded tin plated copper wire (AWG 26, for example) for inner conductor 20. The existing insulation of the copper wire may be increased in diameter by means of a thin wall plastic tube of PTF to form core 18 The outer surface of the tube or core 18 is coated with a conductive ink or paint, such as silver, to provide the outer conductor 16 of a two conductor 50 ohm transmission line system. Etching of the tube may be required to insure adhesion of the silver paint The gap locations 5 are not covered with the conductive ink because they are masked off during the paint application process. A uniform PTF coating 14 is then applied over the entire distal section B-E. The proximal section A-B is formed in a similar manner, except that prior to application of coating 14, a dielectric sleeve or coating 26 of appropriate dielectric constant and loss tangent is placed around the conductive ink 16 located at the proximal section. The dielectric material may preferably be polyacrylamide, titanium dioxide or glucose (see "The Polyacrylamide as a Phantom Material for Electromagnetic Hyperthermia Studies." M. G. Bini, et al., *IEEE Transactions of Biomedical Engineering*, Vol. BMD-31, No. 3, March 1984) from which the appropriate dielectric constant may be calculated for the proper transformer operation using the criterion that the complex propagation constant $k_L$ of the transformer dielectric is the same as the $k_L$ of the distal section. A uniform silver ink coating is then applied over the polyacrylamide material to form a second conductive layer 27. This second conductive layer 27 is present only over the length of the proximal section. It is applied in a manner which creates a short circuit to the silver ink outer conductor 16 at proximal end A but leaves an open circuit between it and the outer conductor 16 at point B.

The outer PTF coating 14 is then applied over the proximal section A-B or continued from the distal section.

This coating 14 permits the probe to operate within wide limits of variations of temperature, tissue dielectric constant and electrical conductivity. A 10 mil thick coating of PTF permits the array to maintain a constant heating pattern (ignoring the effects of heat loss or gain by conduction or convection) for a change in the dielectric constant of tissue from 30 to 80 which may occur during heat application.

Within the dielectric coating 14, fiberoptic thermometry sensors 24 may be embedded. A sensor, such as that produced by the Luxtron Corporation ("16-Channel Fiberoptic Thermometry System with Multisensor Arrays for Thermal Mapping," Wickersheim et al.) may be appropriately modified for application to the array 10. Several linear phosphor sensors 24 about 0.25 mm in diameter (10 mils) may be embedded in the outer dielectric 14. The phosphor sensors 24 utilize the temperature dependence of the fluorescent decay time of the phosphor to determine temperature.

This technique yields a simple, cost-effective multichannel system, which can support a number of small-diameter multi-sensor arrays.

To determine the required value of the load impedance, the proper length of the transformer and its dielectric constant are theoretically determined from the complex propagation constant $k_L$ associated with the current on the antenna, in the manner described below in connection with FIG. 25.

Figure 25:
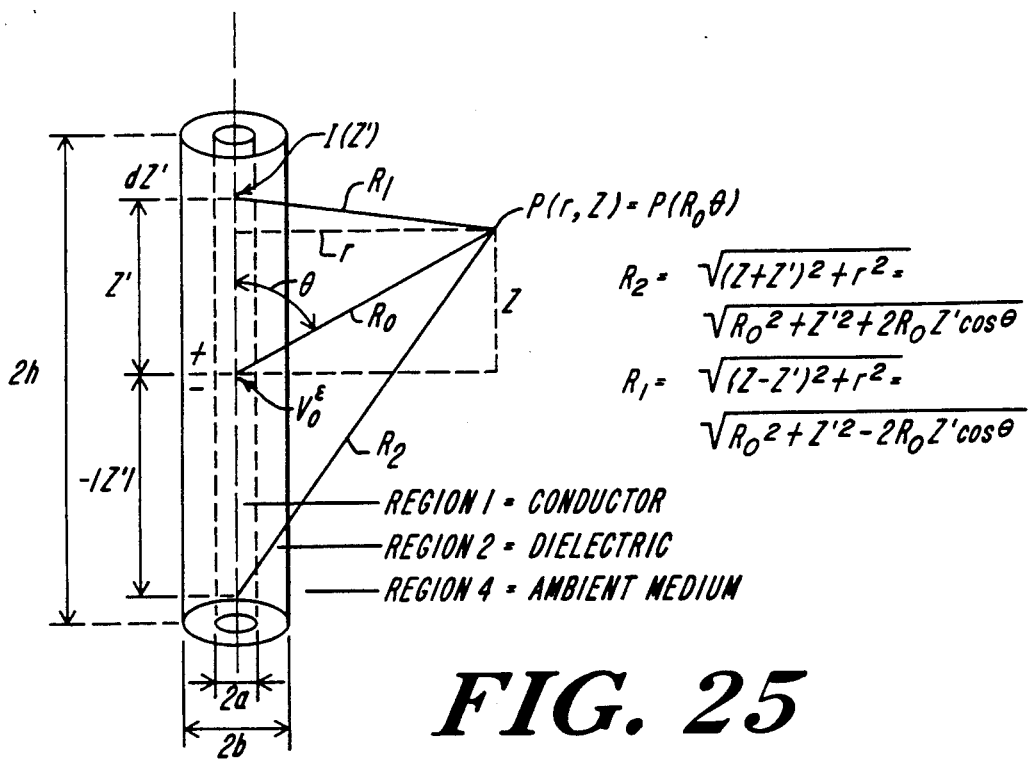
FIG. 25 is an illustration of an insulated dipole in an ambient medium used to depict the algebraic parameters needed for calculating the optimum transformation of parameters.

Consider a simple insulated dipole, FIG. 25, consisting of a central conductor (Region 1) with the half-length "h" and radius "a" surrounded by a cylinder of dielectric which may consist of one (Region 2) or two layers (Region 3)*, with the outer radii "b" and "c", respectively. Outside this insulating sheath is the infinite ambient medium (Region 4) which is lossy or dielectric. The central conductor is sufficiently highly conducting to be well approximated by a perfect conductor. The wavenumbers of the dielectric layers are:

$$k_2 = \omega(\mu_0 \epsilon_2)^{\frac{1}{2}} \text{ and } k_3 = (\omega \epsilon_3)^{\frac{1}{2}},$$

where $\epsilon_2$ and $\epsilon_3$ are the relative dielectric constants of regions 2 and 3, respectively, and are taken to be real since the dielectrics actually used are highly nonconducting and $\mu$ = relative permeability of free space and $\omega$ = the radian frequency. The wave number of the lossy dielectric ambient medium is:

$$k_4 = \beta_4 + i\alpha_4 = \omega(\mu_0 \epsilon_4)^{\frac{1}{2}}, \; \epsilon_4 = \epsilon_4 + i\sigma_4/\omega;$$

wherein $\beta$ = the phase constant in radians/meter; $\alpha$ = the attenuation constant in Nepers/meter and $\sigma$ = the electrical conductivity in Siemens/meter.

The general theory of the insulated antenna applies when the wavenumber of the ambient medium is large compared to that of the insulating sheath and the cross-section of the antenna is electrically small. That is $$|k_4/k_2| 1; \; |k_4/k_3|^2 1; \; (k_2 b)^2 1; \; (k_3 c)^2 1. \quad (1)$$

Subject to these conditions and with the time dependence $e^{-i\omega t}$, the current in the central conductor is $$I(z) = I(0) \frac{\sin k_L(h - |z|)}{\sin k_L h} \quad (2a)$$

-continued $$I(0) = V_o^e Y_o = V_o^e/Z_o$$

where admittance is:

$$Y_o = -(i/2Z_c)\tan k_L h. \quad (2b)$$

For a dielectric with two layers:

$$k_L = k_2 \frac{\ln(c/a) + F^{\frac{1}{2}}}{\ln(c/a) + n_{24}^2 F} \frac{\ln(c/a)^{\frac{1}{2}}}{\ln(b/a) + n_{23}^2 \ln(c/b)} \quad (3)$$

$$Z_c^2 = (\omega\mu_0 k_L^2/2\pi k_2^2)$$
$$[\ln(b/a) + n_{23}\ln(c/b) + n_{24}F] \quad (4)$$

where $n_{23}^2 = k_2^2/k_3^2$, $n_{24}^2 = k_2^2/k_4^2$, and $$F = H_0^{(1)}(k_4 c)/k_4 c H_1^{(1)}(k_4 c);$$

wherein $H_0^{(1)}(k_4c)$ and $H_1^{(1)}(k_4c)$ are zero and first order Hankel functions of the first kind.

These formulas can be simplified by the introduction of an effective wavenumber $K_{2e}$ and an effective permitivity $\epsilon_{2e}$ for an equivalent dielectric composed of a single layer with the outer radius c, viz, $$k_{2e} = k_2 \frac{\ln(c/a)^{\frac{1}{2}}}{\ln(b/a) + n_{23}^2\ln(c/b)} \quad (5)$$

$$\epsilon_{2e} = 2 \frac{\ln(c/a)^{\frac{1}{2}}}{\ln(b+a) + n_{23}^2\ln(c/b)}$$

With (5), the above formulas become $$k_L = k_{2e} [\ln(c/a) + F]^{\frac{1}{2}} [\ln(c/a) + n_{24}^2 F]^{-\frac{1}{2}} \quad (6)$$

$$Z_c = (\mu_0 k_L/2\pi k_2^2) [\ln(c/a) + n_4^2 F] \quad (7)$$

where $n_{2e4}^2 = k_{2e}^2/k_4^2$.

Equation (3) is the complex wave number for current on the surface of cylindrical structures embedded in electrically lossy media, such as tumors.

The input impedance of the bifurcated coaxial line matching transformer is given on page 59 of therefer- ence "Embedded Insulated Antennas for Communication and Heating," by R. W. P. King et al., *Electromagnetics*, Vol. 1, Number 1, January-March 1981. The phase constant of the dielectric inside the transformer must match with $\beta_L$, and $\beta_L d \simeq \pi/2$ gives the required length of the transformer $\beta_L$ is the real part of $k_L$ of Equation 6. The transformer length is the length of the proximal section. Proper impedance matching of the collinear antenna array is therefore dependent on the value of $k_L$. For the proper choice of dielectric inside the transformer and length of transformer, a high value of impedance will exist at the input (Section B). This will effectively isolate the array from the feed line, and with the proper location of the input of the transformer from gap 5, give a collinear array which is properly matched to the 50 ohm feed line.

Figure 26:
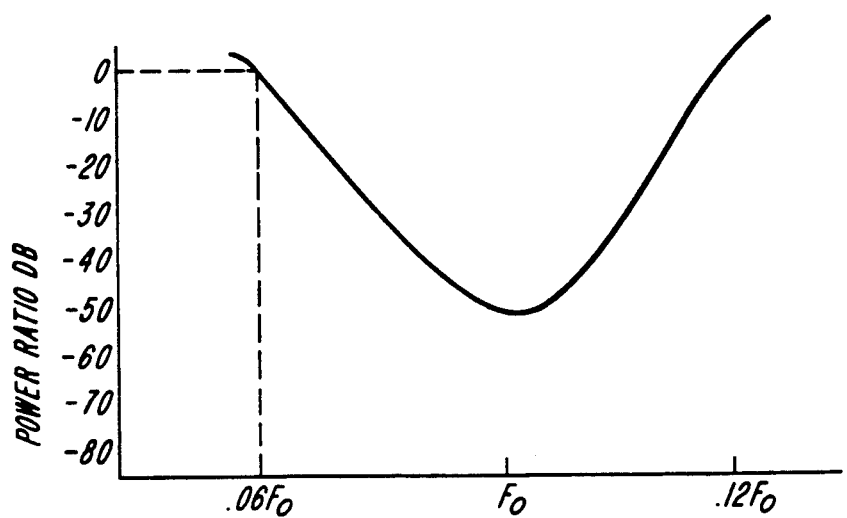
FIG. 26 is a plot of frequency versus power ratio in decibels for the antenna of the invention.

FIG. 26 shows the ratio of reflected power ($P_r$) to transmitted power ($P_t$) in decibels in the coaxial line for a 10 cm long, 3 gap, collinear array of 2 millimeter diameter made in accordance with the invention. The frequency of is the frequency which yields the highest value of terminating impedance for the array wherein the elements of the array are harmonically related. For the 10 cm device in the example, the collinear array that achieves the uniform heating pattern consists of the elements depicted in the distal section B-E of FIG. 20, wherein the frequency is 915 megahertz. The transformer length is about 1 centimeter with a PTF dielectric inside the transformer, having a dielectric constant of 40.

As shown in the optional embodiment of FIG. 27, a lossy sleeve 80 comprised of ferrite cores or beads formed in the shape of a cylinder with an inner bore may be disposed about the applicator 10 at the distal end thereof. Preferably, the inner diameter of the bore in sleeve 80 forms a press fit with the outer diameter of the applicator 10 and is held in place along the longitudinal length of the applicator by a suitable adhesive or other means. The sleeve may be used to modify the heat distribution near and around the applicator 10. We have found that by placing ferrite sleeves 80 around the antenna 10, a significant increase in heat close to the antenna and adjacent to the sleeve is produced for the same power level into the collinear antenna array applicator 10 as compared to an applicator without the sleeve. The electromagnetic fields generated by the antenna applicator 10 produce currents in the ferrite material of sleeve 80 and the resultant heat is transferred by conduction to the surrounding tumor. Significantly less input power to create hyperthermia range temperatures near the applicator (40°–44.5° C.) is required (1–2 watts as compared to 5 watts). The ferrite sleeve 80 therefore creates a source of heat for the tumor that is not dependent on the electrical properties of the tumor. Use of this sleeve provides a source of highly localized heat without requiring an electromagnetic energy absorption capability of tissue. The sleeve may also be used in conjunction with electromagnetic power dissipation in tissue to provide complex heat distribution patterns that conform to the tumor geometry. The Curie temperature of ferrite material determines the upper temperatures beyond which the material becomes non-magnetic and hence non lossy. By selecting an appropriate Curie temperature for the ferrite sleeve, an upper limit on the temperature produced by the sleeve can be established.

An alternate embodiment for the extreme distal end of the applicator is shown in FIGS. 28 and 29, wherein like items in FIG. 20 retain their numeral reference in FIGS. 28 and 29 As may be seen more clearly in FIG. 29, in this embodiment the outer conductor 16 of the antenna array is terminated by a radially inwardly extending ring, shown as sections 16a and 16b. A beam steering resistor 22 may be disposed along the longitudinal axis of the antenna in the path of inner conductor 20, as shown. Alternatively, an equivalent beam steering resistor 21 may be formed as a circular ring embedded in outer insulator 14.

The inner walls of ring sections 16a and 16b are insulated from resistor 22 or (in the event resistor 22 is not present) from inner conductor 20 by dielectric disk 62. The inner conductor is extended radially from the longitudinal axis by disk-like conductor member 18c which is integral with coaxial conductor 18a encased in dielectric 14.

The collinear applicator array 10 may be connected to a commercially available coaxial cable, as shown in FIG. 30, by means of a flexible coaxial connector adaptor 60. This type of connector will eliminate the need to use expensive commercially available SMA connectors.

In addition, the size of SMA connectors may be excessive in diameter for certain applications, thereby creating the need for a special connector whose diameter will conform to the diameter of the collinear applicator.

As shown in FIG. 30, the adaptor comprises a laminated metal conductive ring 40 or ferrule having an inner diameter conforming to the outer diameter of the outer conductor 16 of applicator 10 affixed around the outer conductor. The adaptor of FIG. 30 may be located at various positions along the transmission line. The outer conductor 16, dielectric core 18 and inner conductor 20 of applicator 10 are allowed to extend longitudinally outward from the proximal end of the applicator, with the core 18 extending beyond the outer conductor 16 and the inner conductor 20 extending beyond the core 18. An insulative sleeve 64 is affixed around the extension of core 18. An adaptor pin 42 is secured around the extension of inner conductor 20 to provide an enlarged transition from the outer diameter of inner conductor 20 to the outer diameter of standard coaxial cable inner conductors. For example, the outer diameter of inner conductor 20 is preferably about 0.01", the outer diameter of pin 42 is 0.018" and the outer diameter of sleeve 64 is 0.05".

Pin 42 is adapted to be inserted into tapered bore 51 formed within the inner conductor 50 of a standard SMA cable inner conductor having an outer diameter of 0.045".

Dielectric insulator sleeve 64 is adapted to extend into coaxial channel 53 around inner conductor 50. The metal connector shell of the standard coaxial line slides over sleeve 64 and abuts ring 40. Conductive plastic elastomeric extrusion 44 is bonded at one end by conductive epoxy to shell 46 and is held to ring 40 by friction.

The applicator of the invention can be made as described above with an outer diameter ranging from about 0.05 "to as small as 0.02". With this small diameter, the applicator can be placed almost anywhere within a patient, with or without fiber optics, using current techniques and equipment, such as endoscopes, CT scanners, ultrasound imaging systems, and fluoroscopy units.

For example, in the hyperthermia treatment of urinary tract problems, access to this anatomic system for placement of the applicator could be obtained by any one of the following commonly practiced procedures:

1. Angiographic techniques for access to arterial or venous components (using fluoroscopy);

2. Endoscopic techniques for access to the urethra, prostate, bladder, ureters, and renal pelvis via retrograde cannulation (using fiber optic endoscopy, i.e., cyrtoscopes);

3. Percutaneous techniques for direct access by way of so-called antegrade nonsurgical approach through the flank or back to the renal pelvis; ureter and bladder (using CT, ultrasound, fluoroscopic or even endourologic equipment)

The currently available state-of-the-art imaging equipment (particularly ultrasound and CT) allows visualization and direct puncture of masses in the neck, abdomen, pelvis, and extremities. Under ultrasonic or CT guidance, long, small diameter needles (18-23 gauge) are easily introduced through the skin and into superficial or deep lesions. In a similar manner, the applicator probe 10 could be easily introduced into these lesions through any number of widely available biopsy needles.

The same techniques and equipment can be used for the relatively non-invasive (i.e., non-surgical) access and treatment of other anatomical sites. For example, the gastrointestinal tract, specifically, the biliary system, is routinely approached by endoscopic means (ERCP-endoscopic retrograde cannulation of the pancreas), as well as percutaneously by direct intercostal puncture and catheterization of the liver and bile ducts for diagnosis and treatment of malignant and benign obstructions (due to hepatic, biliary, pancreatic, and lymph node diseases). Other lesions of the GI tract, such as in the stomach, are now approached through gastroscopy. The relatively large size of the endoscope easily allows passage of a probe of the present size The small OD size of this probe, moreover, lends itself to intraoperative use, as is now being performed with small ultrasound probes in certain neurosurgical procedures.

Brain tumors are a potential area for application of the present probe in which hyperthermia may be able to play an immediate and important role. Brain tumors are frequent in the population and histological types with extremely poor prognosis can be identified. Failure to control local disease and not distant metastasis is by far the most frequent cause of death, and clinical trials may be initiated with patients who have failed other modalities (surgery, radiation therapy, chemotherapy). In addition, relatively non-invasive techniques (such as through a burr hole) to guide placement and to monitor results are applicable. The lossy sleeve embodiment of FIG. 27 is capable of use for dissolving arterial plaque specifically for use in angiosurqery.

There has now been described herein a number of different embodiments of the invention, as well as specific embodiments of the collinear array antenna. As indicated previously, the antenna is in the form of a radiation structure that may be used for heating plaque at radio frequencies or microwave frequencies. The structure is used in conjunction with balloon angioplasty. The radiation structure may be considered as in the form of a transmission line system located inside the balloon, such as is illustrated in FIG. 1 herein. The radiation structure is connected to a flexible miniature transmission line of coax type that carries the electromagnetic power from the generator thereof to the balloon structure. The transformer section of the collinear array antenna, such as illustrated in FIGS. 11 and 20, is employed to ensure good impedance matching and no antenna current leakage along the outer surface of the outer conductor of the coax line. Various forms of transmission line structure may be employed inside the balloon or on the inside surface of the balloon, or even between two balloons, one inside the other.

The radiating transmission line structure within the balloon may be a simple two wire arrangement, or may employ multiple wire combinations connected together so that the electric field of the wires extends into the plaque, thus avoiding the heating of artery tissue. In another arrangement, a leaky coax wire may be of various cross-sectional geometries. They may be, for example, microstrip or strip line, as illustrated hereinbefore.

By varying the spacing between these conductors, the number of conductors employed, and the electrical phasing of each conductor, a specific electric field distribution can be achieved in the plaque region. In this regard, refer to the previously described FIG. 6 that shows antenna elements. Also refer to FIG. 13. Thus, in addition to the use of wires, one can use several collinear array antennae, as illustrated in FIG. 6. For example, if four collinear array elements are used, forming a square pattern, and the elements are spaced one-half wavelength apart, current phasings of 0°, 90°, 270°, and 360° or 0° will place the resultant heating pattern in the center of the square.

For the transmission line system illustrated in FIG. 31 herein, the resultant heating pattern is larger, or, in other words, the electric field extends outside the square to a greater extent in comparison to the phasing illustrated in FIG. 32 herein. In this regard, FIG. 31 shows a transmission line system employing four wires within the balloon, with diagonal wires in phase. FIG. 32, on the other hand, shows a transmission line system employing five wires with diagonal wires in phase.

In accordance with a further version of the present invention, there is now described herein a further concept for the radiation structure disposed in the balloon. Again, the system may be used in conjunction with balloon angioplasty. The radiation structure is located within or on the surface of the balloon and is in the form of a helix connected through a balun to the coaxial transmission line. The helical antenna may consist of a single conductor or multiple conductors wound into a helical shape. In this regard, refer to embodiments previously described in FIGS. 3 and 4.

One of the advantages of the helical antenna structure for balloon angioplasty is that with proper design constraints and choice of frequency, the antenna structure can be made to radiate radially outward through the balloon, with little radiation energy directed inward, toward the balloon's center. Hence, the balloon may be inflated with electrically lossy fluid without loss in radiation power that is coupled to the plaque. Other advantages include the ability to alter radiation patterns (normal mode, axial mode and conical mode) such as by changing frequency for a particular design Also, the helical arrangement is mechanically simple to fabricate, and its shape can be made to exactly match the internal shape of the balloon when fully inflated. Also, the helical antenna structure, which may be in wire or collinear array antenna form, can be made mechanically flexible inside the balloon. Although the helix can radiate in several modes, the most commonly used modes for antenna practice are the axial and normal modes. The axial mode provides maximum radiation along the helix axis. It occurs when the helix circumference is on the order of one wavelength. The normal mode, which yields radiation broadside to the helix axis, occurs when the helix diameter is small with respect to the wavelength. Higher order radiation modes are also possible. For example, when the helix dimensions exceed those required for the axial mode, higher order radiation modes exist. The resultant pattern is referred to as a conical or multi lobed pattern. It is this mode of radiation that is insensitive to structures or materials located inside the helix.

Figure 34:
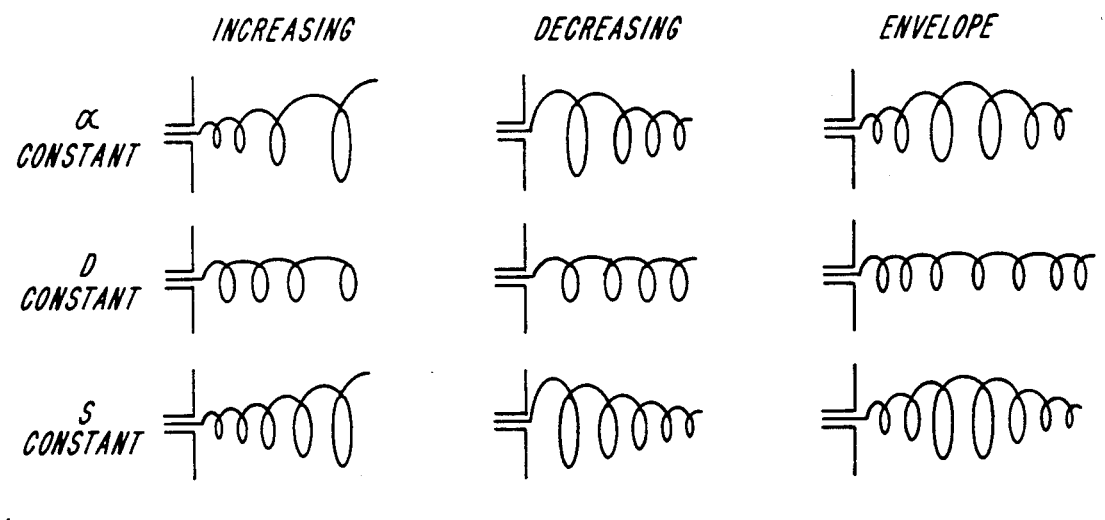
FIG. 34 illustrates various tapered axial mode helical antennae.
Figure 35:
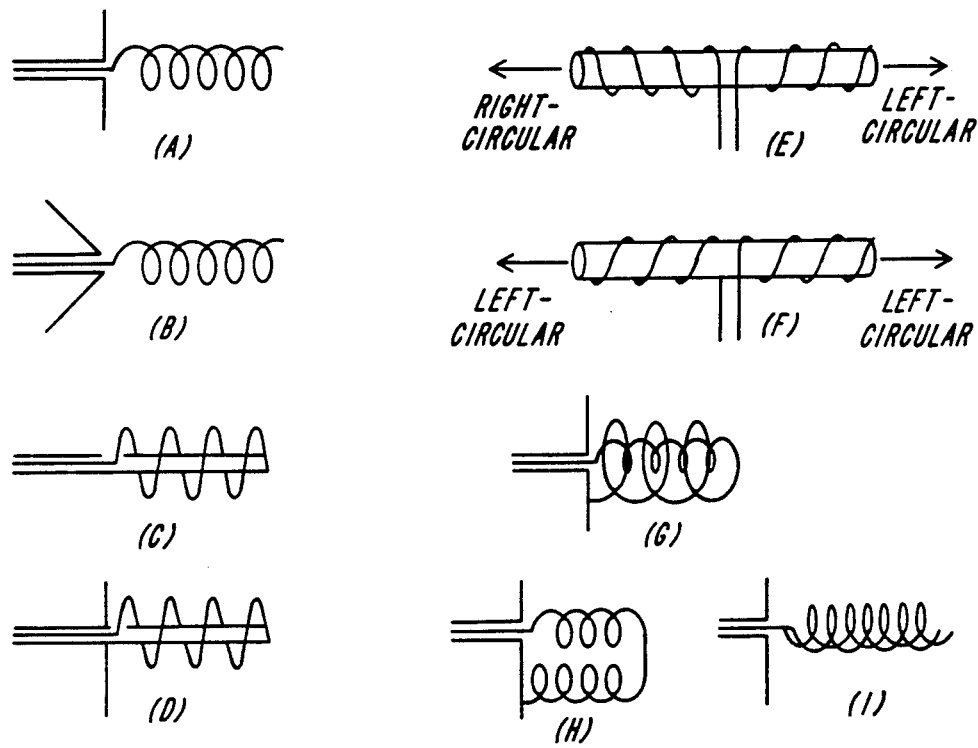
FIG. 35 illustrates axial mode helices.

The basic radiation patterns for free space helices are shown in FIG. 31. The basic helix geometry is also indicated. The pertinent design parameters for a free space environment are:
D = diameter of helix (center to center)
C = circumference
S = spacing between turns
$\alpha$ = pitch angle
N = number of turns
L = axial length of helix
d = diameter of helix
l = length of one turn The helix antennae can be designed with bifilar, quadrifilar or multifilar windings. They can be designed with non-uniform diameters and tapered diameters. Various types of tapered designs are shown in FIG. 34. The envelope taper with either constant pitch angle or constant spacing between turns represents a design shape suitable for balloon application. Various possible constructional and feed arrangements are shown in FIG. 35 herein. In the balloon angioplasty application, the vertical ground plane between the coax and helix is absent. It can be replaced with a transformer section as illustrated hereinbefore in FIG. 20.

In accordance with the present invention, a transmission line is proposed, particularly for microwave balloon angioplasty applications, that is small in diameter and flexible enough to fit inside a catheter lumen. It is comprised of a wire center conductor and a cylindrical dielectric sheath. The outer conductor is constructed of a thin film of highly conductive material, such as silver, loaded in an epoxy resin or elastomeric material and coated over the dielectric sheath. A solid thin strip of metal such as copper is then wrapped continuously along the length of the structure, forming a helix. The thin metal conductor may be a mil or so in thickness and 200 or so mils wide. The design parameters previously set forth above, along with the conductor width, are chosen to provide a low insertion loss, fifty ohm characteristic impedance line. The gaps between turns are essentially shorted out by the conductive ink or thin film.

Figure 36:
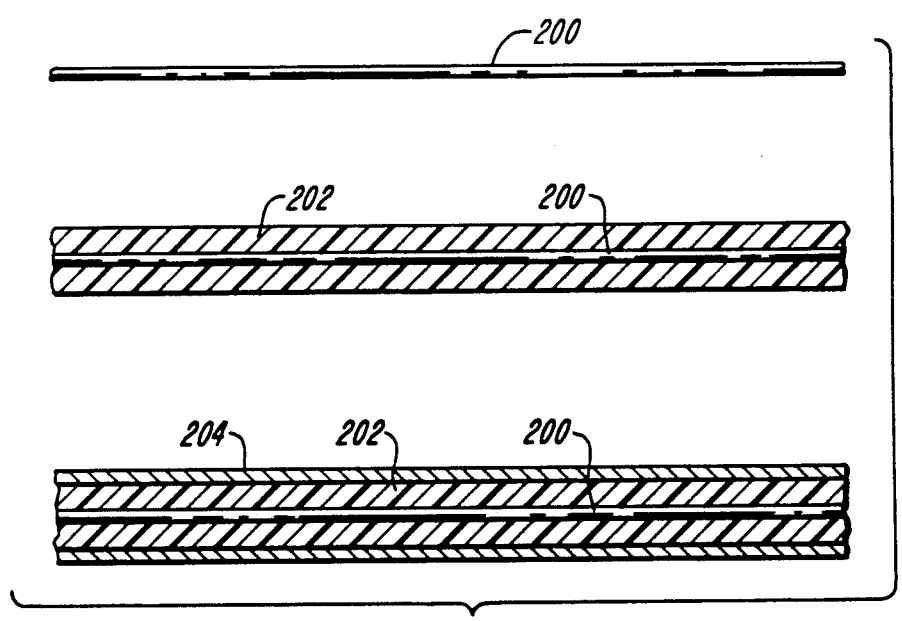
FIG. 36 illustrates a further embodiment of antenna construction.

Without the conductive ink coating and with the dielectric sheath and center conductor, this arrangement is basically a "leaky" coaxial transmission line. The leaky portion is located within the balloon only, and the remaining part contains the conductive ink between turns, and the entire system is suitable for microwave angioplasty. An alternate method of creating the thin conductive film underneath the metal helix is to use well developed thin film process technology. The material (metallic) is sputtered or evaporated onto the dielectric sheath. The thin film process technology application is illustrated herein in FIG. 36. FIG. 36 shows the center conductor wire 200. The wire 200 is then coated with a dielectric material, as indicated at 202. On the dielectric material there is then evaporated or sputtered a thin metallic film forming the outer conductor as indicated at 204 in FIG. 36. The deposition of the outer layer may be by physical vapor deposition or by chemical vapor deposition (CVD).

The next step is to preferably wrap a metal helix on the coax cable for improved insertion loss and mechanical integrity. Dielectric materials may be deposited on the cable to create the aforementioned transformers.

Having now disclosed a number of embodiments of the present invention, it should be apparent to those skilled in the art that numerous other embodiments and modifications thereof are contemplated as falling within the scope of the present invention as defined by the appended claims

What is claimed is:

1. A microwave catheter system for heating arterial plaque, comprising: a flexible catheter member having a distal end and a proximal end, and adapted for positioning in an artery, an inflatable balloon supported at the distal end of the catheter member, a microwave signal generator at the proximal end of the catheter member, transmission line means for transmitting energy coupled from said signal generator through said catheter member and including at the distal end thereof an antenna means for radiating energy substantially uniformly and controllably into said artery, optic fiber means for transmitting optical energy extending through said catheter member between proximal and distal ends thereof and having one end thereof disposed in said balloon in juxtaposition with said antenna means, and channel means extending through said catheter member between proximal and distal ends thereof for coupling a fluid to said balloon for inflation thereof.

2. A microwave catheter system for heating arterial plaque as set forth in claim 1, wherein said channel means has an entrance port to said balloon, and further including a pressurized fluid source coupled to said channel means for introducing the fluid to the balloon under pressure.

3. A microwave catheter system for heating arterial plaque as set forth in claim 2 further including means for exciting the signal generator for a predetermined period of time upon injection of said inflating fluid.

4. A microwave catheter system for heating arterial plaque as set forth in claim 3 wherein said optic fiber means has a sensor at the distal end within the balloon to measure temperature in the balloon or at the surface of the balloon.

5. A microwave catheter system for heating arterial plaque as set forth in claim 4 including a pair of sensors coupled to said fiber means for measuring temperature at two locations within the balloon.

6. A microwave catheter system for heating arterial plaque as set forth in claim 1 wherein said antenna means comprises a collinear array of antennae.

7. A microwave catheter system for heating arterial plaque as set forth in claim 6 wherein the collinear array antennae is disposed inside the balloon.

8. A microwave catheter system for heating arterial plaque as set forth in claim 6 wherein said balloon has a skin and the collinear array antennae is disposed within the skin forming the balloon.

9. A microwave catheter system for heating arterial plaque as set forth in claim 6 wherein the collinear array antennae is formed in a spiral to provide full balloon circumferential coverage.

10. A microwave catheter system for heating arterial plaque as set forth in claim 6 wherein the collinear array antennae is formed in a helix to provide full balloon circumferential coverage.

11. A microwave catheter system for heating arterial plaque as set forth in claim 6 wherein said collinear array antennae includes separate antenna sections and further includes power divider means for intercoupling from the transmission line means to the separate antenna sections.

12. A microwave catheter system for heating arterial plaque as set forth in claim 11 wherein said balloon has a skin and the separate antenna sections are disposed in opposite locations in the balloon skin.

13. A microwave catheter system for heating arterial plaque as set forth in claim 1 wherein said antenna means comprises a plurality of collinear array antennae.

14. A microwave catheter system for heating arterial plaque as set forth in claim 13 wherein said transmission line means further comprises separate transmission lines in the catheter member for delivering electrical energy to each of the collinear array antennae.

15. A microwave catheter system for heating arterial plaque as set forth in claim 1 wherein said antenna means comprises a microstrip radiator.

16. A microwave catheter system for heating arterial plaque as set forth in claim 15 wherein said microstrip radiator is comprised of a conductive strip and a ground plane inter-separated by a dielectric substrate.

17. A microwave catheter system for heating arterial plaque as set forth in claim 15 wherein said radiator is of annular configuration, having an outer radiating strip.

18. A microwave catheter system for heating arterial plaque as set forth in claim 15 wherein said radiator includes a hollow member coated with a thin conductive film to form a ground plane, a thin dielectric film over the ground plane, and a conductive antenna pattern printed over the dielectric film surface.

19. A microwave catheter system for heating arterial plaque as set forth in claim 18 wherein said antenna pattern is in a spiral form.

20. A microwave catheter system for heating arterial plaque as set forth in claim 1 wherein said transmission line means has a center conductor of sufficient stiffness to form a guide wire.

21. A microwave catheter system for heating arterial plaque as set forth in claim 20 including impedance matching means along said center conductor at the location where the center conductor enters and leaves the balloon.

22. A microwave catheter system for heating arterial plaque as set forth in claim 21 wherein the transmission line means has an outer conductor except at positions within the balloon, a tip of the center conductor extending beyond said balloon.

23. A microwave catheter system for heating arterial plaque as set forth in claim 1 wherein said antenna means comprises a plurality of metallic filaments each having a resonant length at the microwave frequency of operation.

24. A microwave catheter system for heating arterial plaque as set forth in claim 23 including an active antenna in the balloon for exciting the filaments.

25. A microwave catheter system for heating arterial plaque as set forth in claim 24 wherein the filaments are disposed inside the balloon.

26. A microwave catheter system for heating arterial plaque as set forth in claim 24 wherein the filaments are disposed within the skin of the balloon.

27. A microwave catheter system for heating material plaque as set forth in claim 1 wherein said balloon has an inside surface and said antenna means is comprised of a plurality of spacedly disposed antenna wires arranged about the balloon near the inside surface thereof and commonly coupled to said transmission line means.

28. A microwave catheter system for heating arterial plaque as set forth in claim 1 wherein said optic fiber means comprises a fiber core and said transmission line means comprises multiply deposited layers on said core including a conductive layer defining an inner conductor, a dielectric coating defining an insulating layer and an outer conductive layer defining an outer conductor.

29. A microwave catheter system for heating arterial plaque as set forth in claim 1 wherein said balloon has a skin and is constructed of a compliant material loaded with a lossy material to allow the balloon skin to absorb microwave energy directly.

30. A microwave catheter system for heating arterial plaque as set forth in claim 1 wherein said balloon is coated with a lossy material to absorb microwave energy.

31. A microwave catheter system for heating arterial plaque as set forth in claim 29 wherein the lossy material includes ferrite or graphite material.

32. A microwave catheter system for heating arterial plaque as set forth in claim 1, wherein said antenna means comprises a helical antenna.

33. A microwave catheter system for heating arterial plaque as set forth in claim 32, wherein said helical antenna is tapered.

34. A microwave catheter system for heating arterial plaque as set forth in claim 1, wherein said antenna means comprises a segment of transmission line within said balloon.

35. A microwave catheter system for heating arterial plaque as set forth in claim 34, wherein a section of said transmission line within the balloon is comprised of a center conductor, a dielectric material disposed about the center conductor and a thin metallic film deposited over the dielectric material and forming an outer conductor.

36. A microwave catheter system for heating arterial plaque as set forth in claim 35, wherein the thin metallic film is deposited by physical vapor deposition.

37. A microwave catheter system for heating arterial plaque as set forth in claim 35, wherein the thin metallic film is deposited by chemical vapor deposition.

38. A device for heating arterial plaque having a proximal section adapted to be coupled to a source of electromagnetic energy and a distal section for radiating said energy, comprising: a collinear array antenna formed by a continuous inner conductor, and a distal end in the distal section surrounded by dielectric material and an interrupted coaxial outer conductor longitudinally extending at one end from the proximal section to another end at the distal section and wherein the interruptions are in the form of circumferential gaps periodically spaced along the coaxial conductor at interrelated harmonic wavelengths to radiate a substantially uniform beam pattern of electromagnetic energy about the periphery of the antenna and an impedance matching means at the proximal section for matching the impedance of the antenna to the impedance of the source of electromagnetic energy, a catheter member supporting at a catheter member distal end an inflatable balloon and further comprising an impedance matching means at a distal side of said balloon for reducing current leakage outside said balloon at said catheter member distal end, said balloon enclosing said collinear array antenna.

* * * * *